United States Patent
Lockridge et al.

(10) Patent No.: US 7,749,284 B2
(45) Date of Patent: Jul. 6, 2010

(54) OXIDATIVE HAIR DYE COMPOSITIONS, METHODS AND PRODUCTS

(75) Inventors: Jennifer Lockridge, New Brighton, MN (US); Cindy L. Orr, Blaine, MN (US); Darcy Lyn Prater, Buffalo, MN (US); Vilis Zaeska, Minneapolis, MN (US)

(73) Assignee: Aveda Corporation, Blaine, MN (US)

( * ) Notice: Subject to any disclaimer, the term of this patent is extended or adjusted under 35 U.S.C. 154(b) by 239 days.

(21) Appl. No.: 12/110,784

(22) Filed: Apr. 28, 2008

(65) Prior Publication Data

US 2009/0265865 A1 Oct. 29, 2009

(51) Int. Cl.
*A61Q 5/10* (2006.01)
(52) U.S. Cl. ..................... 8/405; 8/583; 8/613
(58) Field of Classification Search .............. 8/405, 8/583, 613
See application file for complete search history.

(56) References Cited

U.S. PATENT DOCUMENTS

| | | | |
|---|---|---|---|
| 4,875,902 A | 10/1989 | Grollier et al. | |
| 5,686,082 A | 11/1997 | N'Guyen | |
| 5,843,193 A | 12/1998 | Hawkins et al. | |
| 6,099,591 A | 8/2000 | Matravers et al. | |
| 7,078,545 B1 | 7/2006 | O'Lenick, Jr. et al. | |
| 7,090,872 B2 | 8/2006 | Nagamine et al. | |
| 7,094,432 B2 | 8/2006 | Reinhart et al. | |
| 7,157,104 B1 | 1/2007 | O'Lenick, Jr. et al. | |
| 7,157,105 B1 | 1/2007 | LaVay et al. | |
| 7,172,632 B2 | 2/2007 | Smith et al. | |
| 7,223,775 B2 | 5/2007 | Nishimura et al. | |
| 2002/0016998 A1* | 2/2002 | Pruche et al. ............. | 8/401 |

OTHER PUBLICATIONS

PCT International Search Report; International Application No. PCT/US2009/040594; Completion Date: Nov. 30, 2009; Date of Mailing: Nov. 30, 2009.
PCT Written Opinion of the International Searching Authority, Or the Declaration; International Application No. PCT/US2009/040594; Completion Date: Nov. 30, 2009; Mailing Date: Nov. 30, 2009.
http://www.gnpd.com/Glycerine Soap; Record ID: 270768; Woolworths; Woolworths Earth; Soap & Bath Products; Bar Soap; South Africa; May 11, 2004.
http://www.gnpd.com/Night Nutrition Renewal Crème; Record ID: 10181587; Gurwitch Bristow; Laura Mercier Skincare; Skincare; Face/Neck Care; United States; Aug. 14, 2004.
http://www.gnpd.com/Deep-Cleaning Soothing Mask; Record ID: 757812; ESPA International; ESPA Men; Skincare; Face/Neck Care; United Kingdom; Aug. 20, 2007.
http://www.gnpd.com/Deodorant; Record ID: 10194301; Levlad; Nature's Gate Organics Fruit Blend; Deodorants; Deodorants; United States; Nov. 1, 2004.
http://www.gnpd.com/Rejuvenating Shampoo; Record ID: 665127; Levlad; Nature's Gate Organics Fruit Blend; Haircare; Shampoo; New Zealand; Feb. 23, 2007.

* cited by examiner

*Primary Examiner*—Eisa B Elhilo
(74) *Attorney, Agent, or Firm*—Julie M. Blackburn

(57) ABSTRACT

Oxidative hair dye compositions containing at least one antioxidant botanical extract operable to inhibit the oxidative degradation of one or more oxidative dyes present in the oxidative dye composition, methods for coloring hair, and methods and products that enable multiple use oxidative dye containers.

25 Claims, No Drawings

OXIDATIVE HAIR DYE COMPOSITIONS, METHODS AND PRODUCTS

TECHNICAL FIELD

The invention is in the field of oxidative hair dye compositions, methods for coloring hair and related products.

BACKGROUND OF THE INVENTION

There are basically three types of hair color: temporary, semi-permanent, and permanent. Temporary hair color includes the so-called rinses that individuals use to color their hair for a one day event (e.g. red hair on Valentines day) and typically wash out with one shampoo. Semi-permanent hair color is used by individuals who desire to color their hair for a longer period of time. Typical semi-permanent hair color washes out after six to twenty four shampoos. Permanent, or oxidative, hair color provides permanent color that does not wash out with shampooing. Both temporary and semi-permanent hair color are direct application—that is the hair color is applied directly to the hair and will impart color immediately. The unused hair color can be saved and used again for other applications. Most individuals who color their hair use oxidative hair color in either a retail kit or salon environment. The oxidative hair color process involves mixing a separately stored oxidative dye composition with an aqueous based oxidizing agent, then immediately applying the mixture to the individual's hair for a period of time necessary to color the hair, usually from 5 to 80 minutes. The oxidative dye composition reacts with the aqueous based oxidizing agent to form colored dye molecules once they are absorbed into the hair shaft and impart color. The dye mixture thus obtained is very labile and must be applied to the hair very shortly after it is prepared. In fact, even an oxidative dye composition alone with time will even erode the effectiveness of the oxidative dye composition alone, even before it has been combined with the oxidizing agent. The extreme instability of oxidative dyes creates problems for hair salons where oxidative hair dye procedures are a major segment of their business. In a typical salon environment the oxidative dye composition is stored in containers such as tubes. The salon has many different colors of dye to facilitate mixing colors to provide the customer with the desired hair color. In most instances only a small fraction of the oxidative dye in the container is used in one procedure, and the remaining oxidative dye composition is stored for later use in other applications. However, due to the instability of the dye compositions under regular atmospheric conditions, they will sometimes be rendered ineffective, or worse yet, be used to dye hair, providing an unsuccessful result and an unhappy customer.

Hair dye manufacturers try to improve the stability of oxidative dye compositions by formulating them with various antioxidants. Ascorbic acid is one commonly used antioxidant. However, it very rapidly loses its activity when exposed to air so that once the dye containers are open the ascorbic acid is no longer an effective antioxidant. The result is that the dyes become rapidly oxidized by air and lose effectiveness. Another typically used antioxidant, sodium dithionate, is sometimes malodorous in addition its propensity for undergoing undesirable secondary reactions with nitro-based dyes. Erythorbic acid is also widely used but exhibits certain undesirable properties. There is a need for antioxidants for use in formulating hair dye compositions that maximize the stability of the oxidative dyes to facilitate multiple uses and interim storage of oxidative dye compositions until depleted. Additionally, it is desirable that such antioxidants be natural ingredients rather than synthetic organic compounds.

It has been discovered that certain antioxidants, specifically those containing at least one flavanoid component and/or at least one phenolic acid component provide excellent antioxidant properties when formulated with oxidative hair dye compositions, facilitating long term storage and multiple uses of the oxidative dye product once the container is opened.

SUMMARY OF THE INVENTION

The invention is directed to an oxidative dye composition comprising one or more oxidative dyes and at least one antioxidant botanical extract operable to inhibit the oxidative degradation of one or more oxidative dyes present in the oxidative dye composition.

The invention is also directed to an oxidative dye composition comprising one or more oxidative dyes and at least one antioxidant comprising at least one flavanoid component and/or at least one phenolic acid component, present in an amount sufficient to inhibit the oxidative degradation of one or more oxidative dyes present in the oxidative dye composition.

The invention further comprises a packaged oxidative hair dye composition comprising one or more oxidative dyes, at least one antioxidant comprising at least one flavanoid component and/or at least one phenolic acid component, in an amount sufficient to inhibit the oxidative degradation of the one or more oxidative dyes present in the composition, and a hermetically sealed oxidation resistant metallic container.

The invention further relates to an oxidative dye composition containing one or more oxidative dyes stabilized against oxidative degradation by an organic antioxidant, wherein at least a portion, preferably all, of the organic antioxidant is replaced with an antioxidant comprising at least one flavanoid component and/or at least one phenolic acid component.

The invention further comprises a method for stabilizing an oxidative hair dye composition comprising one or more oxidative dyes against oxidative degradation, comprising formulating the composition with at least one antioxidant comprising at least one flavanoid component and/or at least one phenolic acid component, in an amount sufficient to stabilize the one or more oxidative dyes present in the composition against oxidative degradation The invention further comprises a method for oxidatively coloring hair comprising applying to the hair an oxidative dye mixture formed by combining an oxidative dye composition and an aqueous oxidizing agent composition, wherein the oxidative dye mixture comprises at least one oxidative dye and at least one antioxidant containing at least one flavanoid component and/or at least one phenolic acid component.

The invention further comprises a method for making a multiple use oxidative dye product comprising an oxidative dye composition containing one or more oxidative dyes in an air tight oxidation resistant package comprising formulating the oxidative dye composition with at least one antioxidant comprising at least one flavanoid component and/or at least one phenolic acid component, in an amount sufficient to inhibit the oxidative degradation of the one or more oxidative dyes to enable the composition in the container to be used more than one time.

The invention further comprises a multiple use oxidative dye product comprising an oxidative dye composition containing one or more oxidative dyes packaged in an air tight oxidation resistant container, said dye composition containing at least one antioxidant comprising at least one flavanoid component and/or at least one phenolic acid component in an amount sufficient to inhibit the oxidative degradation of the one or more oxidative dyes present in the composition.

DETAILED DESCRIPTION

I. The Oxidative Dye Composition

The oxidative dye composition of the invention is generally aqueous based comprising from about 0.01-99%, preferably from about 0.1-98%, more preferably from about 45 to 95% by weight of the total composition of water.

A. The Antioxidant

The oxidative dye composition comprises at least one antioxidant comprising at least one flavanoid component and/or at least one phenolic acid component, present in an amount sufficient to inhibit the oxidative degradation of one or more oxidative dyes present in the oxidative dye composition. The term "antioxidant" means that the components present have antioxidant properties such that the antioxidant is operable to inhibit either in whole or in part the oxidative degradation of one or more of the oxidative dyes present in the dye composition. Preferably such antioxidants contain free radical scavenging ability.

Such amounts may range from about 0.0001 to 35%, preferably from about 0.001-25%, more preferably from about 0.01-20% by weight of the total composition. The antioxidant may be a botanical extract. The term "botanical extract" means that the ingredient is a natural material derived from plants such as trees, flowers, fruits, and so on. More specifically, the extract may be derived from the seeds, fruit, peel, flowers, stems, roots, or any other part of the plant. The plant extract may be prepared by extraction with water, alcohols, or other standard solvents, or by squeezing, pulverizing, or crushing the desired plant part.

In one preferred embodiment the antioxidant contains both flavanoid component and a phenolic acid component. Suitable flavanoids include aspalathin, orientin, iso-orientin, rutin, isoquercetin, vitexin, isovitexin, chryseriol, quercetin, luteolin, nothofagin, or catechin. Suitable phenolic acids include protocatechic acid, caffeic acid, p-hydroxybenzoic acid, vanillic acid, p-coumaric acid, ferulic acid, and the like. More preferably the antioxidant is a botanical extract that contains at least one flavanoid component and at least one phenolic acid component. In one most preferred embodiment, the flavanoid component includes aspalanthin.

Examples of botanical extracts that may contain the phenolic acid and/or flavanoid component include, but are not limited to, extracts from rowanberry, chokecherry, blueberry, saskatoon berry, dark plum, cherry, certain apples, black tea, mulberries, june berries, aloe ferox, quince, etc.

More specifically, the following botanical extracts may be suitable, including but not limited to:

| Botanical Extract | Contains Flavanoid Component | Contains Phenolic Acid Component |
|---|---|---|
| *Aspalanthus Linearis* extract | Yes | Yes |
| Curcumin | No | Yes |
| *Rhus Typhina* (Sumac) leaf extract | Yes | Yes |
| *Camellia Oleifera* leaf extract | Yes | Yes |
| *Pyrus Malus* (Apple) peel extract | Yes | Yes |
| *Epilobium Angustifolium* extract | Yes | Yes |
| *Scutellaria Baicalensis* root extract | Yes | No |
| Tetrahydrocurcumin diacetate | No | Yes |
| Tetrahydrodiferuloylmethane | No | Yes |
| *Vitis Vinifera* (Grape) seed extract | Yes | Yes |

-continued

| Botanical Extract | Contains Flavanoid Component | Contains Phenolic Acid Component |
|---|---|---|
| *Punica Granatum* extract | Yes | Yes |
| *Rosmarinus Officinalis* extract | Yes | Yes |
| Licochalcone | Yes | No |
| *Coffea Arabica* (Coffee) leaf/seed extract | No | Yes |

More preferred are extracts or components thereof that contain both the flavanoid component and the phenolic acid component; such as *Aspalanthus Linearis* extract, *Rhus Typhina* extract, *Camellia Oleifera* extract, *Pyrus Malus* extract, *Epilobium Angustifolium* extract, *Vitis Vinifera* (Grape) seed extract, *Punica Granatum* extract, *Rosmarinus Officinalis*, and the like.

One particularly suitable antioxidant botanical extract is an extract of Rooibos tea or *Aspalanthus Linearis*. This extract contains a significant flavanoid component that includes aspalathin, orientin, iso-orientin, rutin, isoquercetin, vitexin, isovitexin, chryseriol, quercetin, luteolin, nothofagin, or catechin; and a significant phenolic acid component that includes protocatechic acid, caffeic acid, p-hydroxybenzoic acid, vanillic acid, p-coumaric acid, ferulic acid, and the like.

B. Oxidative Dyes

The oxidative dye composition comprises one or more oxidative dyes that are operable, when combined with an aqueous oxidizing agent, to impart color to the hair. Generally such dyes are primary intermediates and, optionally, couplers.

1. Primary Intermediates

Dyestuff components include primary intermediates and, optionally, couplers for the formation of oxidation dyes. Primary intermediates may generally be present in the oxidative dye composition in amounts ranging from about 0.001 to 25%, preferably from about 0.005 to 20%, more preferably from about 0.01 to 15% by weight of the total composition. Such primary intermediates include ortho or para substituted aminophenols or phenylenediamines, such as para-phenylenediamines of the formula:

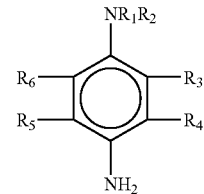

wherein $R_1$ and $R_2$ are each independently hydrogen, C1-6 alkyl, or C106 alkyl substituted with hydroxy, methoxy, methylsulphonylamino, furfuryl, aminocarbonyl, unsubstituted phenyl, or amino substituted phenyl groups;

$R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more amino or hydroxyl groups.

Such primary intermediates include para-phenylenediamine (PPD), 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, and derivatives thereof, and acid or basic salts thereof. Also suitable are various types of pyrimidines such as 2,3,4,5-tetraminopyrimidine sulfate and 2,5,6-triamino-4-pyrimidinol-sulfate.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

2. Couplers

If present, the color couplers may range from about 0.0001-10%, more preferably about 0.0005-8%, most preferably about 0.001-7% by weight of the total oxidative dye composition. Such color couplers include, for example, those having the general formula:

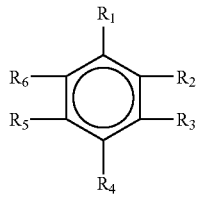

wherein $R_1$ is unsubstituted hydroxy or amino, or hydroxy or amino substituted with one or more $C_{1-6}$ hydroxyalkyl groups; $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group.

Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methylpyrazolone, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene. 6-ethoxy-1-bis(beta-hydroxyethyl)amino-3-aminobenzene, 6-hydroxyethyl-1,3-diaminobenzene, 3,4-methylenedioxyphenol, 3,4-methylenedioxy-1-[(beta-hydroxyethyl) amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamioniphenoxyethanol, and mixtures thereof.

C. Emollient Oils

If desired the oxidative dye composition may contain one or more emollient oils. Such oils will provide a conditioning effect to the hair. If present, such oils may range from about 0.001 to 45% preferably from about 0.01 to 40%, more preferably from about 0.1 to 35% by weight of the total composition. Suitable oils include silicones such as dimethicone, phenyl silicones, fatty alkyl silicones such as cetyl or stearyl dimethicone, or silicone surfactants which are generally referred to as dimethicone copolyols, or cetyl dimethicone copolyol. Also suitable are various animal, vegetable, or mineral oils derived from plants or animals, or synthetic oils. Examples include oils from sunflower, castor seeds, orange, lemon, jojoba, mineral oil, and the like.

D. Surfactants

The oxidative dye composition may comprise one or more surfactants. Suitable surfactants include anionic surfactants, nonionic surfactants, amphoteric surfactants, and the like. If present, surfactants may range from about 0.001-50%, preferably about 0.005-45%, more preferably about 0.1-40% by weight of the first composition.

1. Nonionic Surfactants

Examples of nonionic surfactants include alkoxylated alcohols or ethers, alkoxylated carboxylic acids, sorbitan derivatives, and the like. Alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2-30, which is formed by the reaction of stearyl alcohol and ethylene oxide where the number of repeating ethylene oxide units is 2 to 30; Oleth 2-30 which is formed by the reaction of oleyl alcohol and ethylene oxide where the number of repeating ethylene oxide units is 2 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. Particularly preferred is where the nonionic surfactant is steareth-21.

Also suitable are alkyoxylated carboxylic acids, which are formed by the reaction of a carboxylic acid with an alkylene oxide or with a polymeric ether. The resulting products have the general formula:

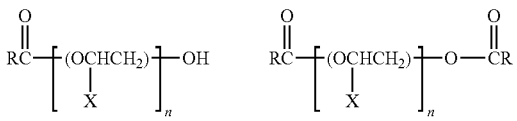

where RCO is the carboxylic ester radical, X is hydrogen or lower alkyl, and n is the number of polymerized alkoxy groups. In the case of diesters, the two RCO— groups do not need to be identical. Preferably, R is a $C_{6-30}$ straight or branched chain, saturated or unsaturated alkyl, and n is from 1-100.

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20-85, sorbitan oleate, sorbitan palmitate, sorbitan sesquiisostearate, sorbitan stearate, and so on. In one preferred embodiment Polysorbate 20 is preferred.

2. Anionic Surfactants

The dye composition may optionally contain one or more anionic surfactants. Preferred ranges of anionic surfactant are about 0.01-25%, preferably 0.5-20%, more preferably 1-15% by weight of the total oxidative composition. Suitable anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula: $R_1—SO_3-M$ wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide, or fatty acids reacts with alkanolamines or ammonium hydroxides. The fatty acids may be derived from coconut oil, for example. Examples of fatty acids also include lauric acid, stearic acid, oleic acid, palmitic acid, and so on.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones, which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula: wherein $R.sub.1$ is a $C.sub.8-24$ alkyl or alkenyl radical, preferably $C.sub.10-18$; $R.sub.2$ is H, $C.sub.1-4$ alkyl, phenyl, or —$CH.sub.2COOM$; $R.sub.3$ is $CX.sub.2-$ or $C.sub.1-2$ alkoxy, wherein each X independently is H or a $C.sub.1-6$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

3. Cationic, Zwitterionic or Betaine Surfactants

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula $R—NH(CH_2)_nCOOM$ or iminodialkanoates of the formula: $R—[(CH_2)_mCOOM]_2$ and mixtures thereof, wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-imino-dipropionic acid, or mixtures thereof.

Zwitterionic surfactants are also suitable for use in the compositions of the invention and include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like. Particularly preferred is cocamidopropylbetaine.

E. Polar Solvents

The oxidative dye composition may also comprise a variety of nonaqueous polar solvents other than water, including mono-, di-, or polyhydric alcohols, and similar water soluble ingredients. If present, such polar solvents may range from about 0.01-25%, preferably about 0.05-15%, more preferably about 0.1-10% by weight of the first composition of polar solvent. Examples of suitable monohydric alcohols include ethanol, isopropanol, benzyl alcohol, butanol, pentanol, ethoxyethanol, and the like. Examples of dihydric, or polyhydric alcohols, as well as sugars and other types of humectants that may be used include glycerin, glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like.

F. Chelating Agents

The oxidative dye composition may optionally contain 0.0001-5%, preferably 0.0005-3%, more preferably 0.001-2% of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include EDTA and calcium, sodium, or potassium derivatives thereof, HEDTA, sodium citrate, TEA-EDTA, and so on.

G. pH Adjusters

It may also be desirable to add small amounts of acids or bases to adjust the pH of the oxidative dye composition to the desired pH range. Suitable acids include hydrochloric acid, phosphoric acid, and the like. Suitable bases include sodium hydroxide, ammonium hydroxide, potassium hydroxide, and the like. Also suitable are primary, secondary, or tertiary amines or derivative thereof such as aminomethyl propanol, monoethanolamine, and the like. Suggested ranges of pH adjusters are from about 0.00001-8%, preferably about 0.00005-6%, more preferably about 0.0001-5% by weight of the total composition.

H. Other Botanical Ingredients

The oxidative dye composition may comprise one or more additional botanical ingredients in addition to the antioxidant botanical ingredient. If present, suggested ranges are from about 0.00001-10%, preferably from about 0.0001-8%, more preferably from about 0.0001-5% by weight of the total composition. Examples of such ingredients include *Camellia Sinensis* extract, *Camellia Oleifera* extract, Vanilla extract, *Aloe Barbadensis* extract, and the like.

II. The Aqueous Oxidizing Agent Composition

The oxidative dye composition of the invention is combined with an aqueous oxidizing agent composition immediately prior to application to hair. This composition contains water, generally in an amount ranging from about 1 to 99.9%, preferably from about 2 to 98%, more preferably from about 3 to 95% by weight of the total composition. In addition, the aqueous oxidizing agent composition also comprises an oxidizing agent that will react with the dyes present in the oxidative dye composition to color the hair. Most often the aqueous oxidizing agent used is hydrogen peroxide, but other peroxides or oxidizing agents may be used such as calcium peroxide. Preferably the hydrogen peroxide concentration in the aqueous oxidizing agent composition ranges from about 10 to 40 volume, that is the amount of hydrogen peroxide that is present in the composition on a volume basis.

The aqueous oxidizing agent composition may contain one or more additional ingredients including but not limited to those set forth in Section I with respect to the oxidative dye composition, and in the same general percentage ranges.

III. The Container

The oxidative dye composition is preferably stored in a container that is air-tight and made of a material that is oxidation resistant. Preferably such containers are in the form of tubes, jars, bottles, and the like. Preferred is where the container is a tube, preferably a tube that can be compressed to dispense the oxidative dye composition found therein. Suitable tubes may be metallic. Preferred is where the tube is an oxidation resistant aluminum. In the most preferred embodiment the tube is made from oxidation resistant aluminum having less than 100 ppm of cadmium, mercury, lead, and hexavalent chromium.

The container must contain a closure that will close the container tightly and prohibit air from oxidizing the contents of the container. A variety of closures are suitable including screw caps, snap off lids, and the like. Preferably the closure is reusable in the even multiple uses are desired.

The invention enables multiple uses of oxidative hair dye compositions in a salon environment. Once the container is opened it may be used to dispense the desired amount of oxidative dye composition as needed by the customer. The container is closed and stored for hours, days, weeks, or even months, before the remaining contents may be used again. An oxidative dye composition formulated according to the invention and stored in a suitable container can be used and the remaining contents stored indefinitely. For example, using the antioxidant will enable the container of oxidative hair to be used and stored from 1-6 days, or from 1 to 3 weeks, or from 1 to 4 months before it is used again.

The invention will be further described in connection with the following examples which are set forth for the purpose of illustration only.

Example 1

Oxidative hair dye compositions were prepared as follows:

| Ingredient | 1 | 2 |
|---|---|---|
| Water | QS100 | QS100 |
| Rooibus Tea Extract (*Aspalanthus Linearis* extract) | — | 1.05 |
| Erythorbic Acid | 0.60 | — |
| Tetrasodium EDTA | 0.50 | 0.50 |
| Sodium Sulfite | 0.50 | 0.50 |
| Glycerine | 4 | 4 |
| Cocamidopropyl betaine | 5 | 5 |
| Cocamide MEA | 5 | 5 |
| Polysorbate 20 | 2 | 2 |
| Glyceryl stearate | 5 | 5 |
| Cetearyl alcohol | 5 | 5 |
| m-aminophenol | 0.033 | 0.033 |
| 1-naphthol | 0.005 | 0.005 |
| p-phenylenediamine | 0.141 | 0.141 |
| Resorcinol | 0.179 | 0.179 |
| p-Aminophenol | 0.068 | 0.068 |
| Ammonium hydroxide | 7 | 7 |

The dye compositions were prepared by combining and heating the dye ingredients to 85° C. until all dyes were dissolved. The mixture was cooled to 80° C. Separately the remaining ingredients were combined and heated to 80° C. with stirring. When both mixtures reached 80° C. the phases were slowly combined and the mixture cooled. The entire batch was cooled to room temperature (25° C.) and poured into tubes.

Yak hair, 4 inch long pieces, was cut into swatches weighing 1.5 grams. 10 grams of hair color formulas 1 and 2 were combined with 10 grams of an aqueous solution of 20 volume hydrogen peroxide developer. Each mixture was applied to the yak hair swatches with a brush and allowed to remain for 30 minutes. The hair was rinsed well with warm water. To each swatch, 5 grams of Aveda Color Conserve shampoo, a commercial product having the following ingredient list:

aqueous (water, aqua purificata, purified) extracts: camellia sinensis extract, citrus aurantium amara (bitter orange) peel extract, astragalus membraceus (milk vetch), root extract, schisandra chinensis fruit extract, pinus tabulaeformis (pine) park extract, vitis vinefera (grape) seed extract, sedum rosea root extract, rehmannia chiensis root extract, ammonium lauryl sulfate, dispdium laureth sulfosuccinate, lauroamidopropyl betaine, cinnamidopropyl dimethylamine, glycol stearate, glycol distearate, polyglyceryl-10 oleate, polyquarternium-7, fragrance, citus labdaniferus oil, glycerin, citric acid, disodium edta, propylparaben methylparaben methylisothiazolinone, methylchloroisothiazolinone was applied to each of the swatches and worked into a lather. The swatches were rinsed with warm water and allowed to dry. Visual observation of the dried swatches revealed that both swatches exhibited the same color and tone, thus demonstrating that the antioxidants of the invention provide similar results as erythorbic acid as regards color deposition.

Example 2

Oxidative dye compositions containing Rooibos tea extract were compared with compositions containing sodium hydrosulfite as an antioxidant, to ascertain whether Rooibos tea containing compositions had any undesired impact on oxidative nitro-based dyes. Compositions were prepared as follows:

(1) 0.02% aqueous solution of HC Blue No. 2
(2) 0.02% aqueous solution of HC Blue No. 2 containing 0.5% sodium hydrosulfite
(3) 0.02% aqueous solution of HC Blue No. 2 containing 0.5% Rooibos tea extract The compositions were placed into glass jars and visually observed. Compositions (1) and (3) were a nearly identical dark blue. Composition (2) was uncolored, showing that the sodium hydrosulfite degrades HC Blue No. 2.

In addition, about 10 grams of each of the above compositions (1), (2), and (3) were applied to swatches of yak hair. The dye was allowed to remain on the hair for twenty minutes, then rinsed off with water. The swatches colored with (1) and (3) showed a nearly identical dark blue color. The swatch colored with (2) showed very poor color deposit. Conclusion: that Rooibos tea does not interfere with nitro-based dyes, while sodium hydrosulfite does interfere with nitro-based dyes.

Example 3

Rooibos tea extract was compared to the standard antioxidant erythorbic acid to measure relative antioxidant activity. The DPPH (2,2-diphenyl-1-picrylhydrazyl) Antioxidant Assay measured in the Fluostar Optima Microplate Reader was used to evaluate antioxidant activity.

In this assay antioxidants with free radical scavenging activity react with the stable free radical DPPH to produce 1,1-diphenyl-2-picrylhydrazine, which provides a very strong absorption band at 517 nanometers that is deep violet in color. The extra electron in DPPH becomes paired off in the presence of an antioxidant with free radical scavenging properties, and the resulting decolorization of the sample is stoichimetric with respect to the number of electrons taken up.

To conduct the test, positive controls were prepared by dissolving 3 mg rutin in 1 ml. DMSO to provide a stock solution "A". Stock solution A was then diluted with DMSO to provide 1.0; 0.75; 0.375; 0.075; and 0.015 mg/ml solutions. DPPH, 6.9 mg. was dissolved in 50 ml reagent alcohol, (HPLC grade, Fisher Scientific #A995-4). This solution was stored in an amber bottle and used on the same day the test was conducted.

Test samples were initially screened for antioxidant activity to ascertain proper concentration for conducting the test by combining 5 microliters of test sample and 95 microliters of DPPH in a plate containing wells. If the composition in the well rapidly turned yellow the initial concentration of the antioxidant in the sample was too high and the sample was diluted 50/50 with DMSO. Then dilutions of test sample in DMSO at 4, 2, 1, and 0.2 mg/ml were prepared.

Solvent blank, 5 microliters, was dispensed into one well and 5 microliters of DMSO into nine wells. Five microliters of the positive control solutions in varying concentrations were placed into wells going from low to high concentration. Each sample was dispensed in triplicate. Then 95 microliters of DPPH solution was added to each well using a multi-channel pipette so that the final volume per well was 100 microliters. The plate was analyzed in a Fluostar Optima Microplate Reader, first warming up the reader to 30° C. prior to scanning the plate according to the machine instructions for the DPPH assay. The free radical scavenging activity of the samples were dispensed from the device as raw data of absorbance values and inserted into an excel spreadsheet. The IC50 values were calculated using the embedded excel spreadsheet calculation feature:

Average Absorbance: mean of triplicate readings
Standard Deviation The square root of the variance
% growth: (average absorbance/average absorbance blank)×100
% inhibition: (100-% growth)
IC50: 10^FORECAST (50, LOG(Concentration),% Inhibition The DPPH values for a variety of tested ingredients are set forth below:

| Ingredient | DPPH value |
|---|---|
| Erythorbic acid | 9.94 |
| *Aspalanthus Linearis* extrat | 5.67 |
| Curcumin | 66.26 |
| *Rhus Typhina* (Sumac) leaf extract | 114.43 |
| Eugenol | 110.93 |
| *Ocimum Sanctum* leaf extract | 88.84 |
| *Camellia Oleifera* extract | 74.07 |
| *Epilobium Angustifolium* extract | 62.15 |
| *Scutellaria Baicalensis* root extract I | 40.18 |
| *Scutellaria Baicalensis* root extract | 31.84 |
| Tetrahydrocurcumin diacetate | 31.29 |
| Tetrahydrodiferuolyolmethane | 23.65 |
| *Vitis Vinifera* (Grape) seed extract | 22.26 |
| *Bombax Malabaricum* flower extract | 17.52 |
| *Punica Granatum* extract | 15.67 |
| *Rosmarinus Officinalis* extract | 11.95 |
| Licochalcone | 11.45 |
| *Jasminum Glandiflorum* (Jasmine) flower extract | 10.99 |
| *Coffea Arabica* (Coffee) leaf/seed extract | 10.13 |

The ingredients having higher DPPH values had the highest amount of free radical scavenging activity, and in the concentrations tested would be the most effective antioxidant replacement for erythorbic acid. The extract concentration can be increased to increase free radical scavenging ability, if desired.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. An oxidative hair dye composition comprising at least one oxidative dyes selected from p-phenylenediamine; p-aminophenol; o-aminophenol; N,N-bis(2-hydroxyethyl)-p-phenylenediamine; 2,5-diaminotoluene; 1-phenylamino-4-aminobenzene; 1-bis(beta-hydroxyethyl)amino-4-aminobenzene; 2,5,6-triamino-4-pyrimidinol sulfate; tetraminopyrimidine; and salts thereof; and at least one antioxidant comprising at least one flavanoid component selected from aspalanthin, orientin, iso-orientin, rutin, isoquercetin, vitexin, isovitexin, chryseriol, quercetin, luteolin, nothofagin, catechin; and/or at least one phenolic acid component selected from protocatechic acid, caffeic acid, p-hydroxybenzoic acid, vanillic acid, p-coumaric acid, ferulic acid; present in an amount sufficient to inhibit the oxidative degradation upon exposure to air of one or more oxidative dyes present in the oxidative dye composition.

2. The oxidative dye composition of claim 1 wherein the antioxidant is in the form of a botanical extract having a DPPH value of greater than or equivalent to that of erythorbic acid.

3. The oxidative dye composition of claim 1 wherein the composition contains at least one flavanoid component and at least one phenolic acid component.

4. The oxidative dye composition of claim 1 wherein the antioxidant comprising at least one flavanoid component is in the form of a botanical extract selected from the group consisting of *Aspalanthus Linearis, Rhus Typhina, Camellia Oleifera, Pyrus Malus, Epilobium Augustifolium, Scutellaria Baicalensis, Vitis Vinifera, Punica Granatum, Rosmarinus Officinalis*, Licochalcone, and mixtures thereof; and the antioxidant comprising at least one phenolic acid component is in the form of a botanical extract selected from the group consisting of *Aspalanthus Linearis*, Curcumin, *Rhus Typhina, Camellia Oleifera, Pyrus Malus, Epilobium Augustifolium*, Tetrahydrocurcumin diacetate, Tetrahydrodiferuloyl methane, *Vitis Vinifera, Punica Granatum, Rosmarinus Officinalis, Coffea Arabica*; and mixtures thereof.

5. The composition of claim 4 wherein the antioxidant is the botanical extract from *Aspalanthus Linearis*.

6. A packaged oxidative hair dye composition comprising at least one oxidative dyes selected from p-phenylenediamine; p-aminophenol; o-aminophenol; N,N-bis(2-hydroxyethyl)-p-phenylenediamine; 2,5-diaminotoluene; 1-phenylamino-4-aminobenzene; 1-bis(beta-hydroxyethyl)amino-4-aminobenzene; 2,5,6-triamino-4-pyrimidinol sulfate; tetraminopyrimidine; and salts thereof, at least one antioxidant comprising at least one flavanoid component selected from the group consisting of aspalathin, orientin, iso-orientin, rutin, isoquercetin, vitexin, isovitexin, chryseriol, quercetin, luteolin, nothofagin, or catechin; and mixtures thereof; and/or at least one phenolic acid component selected from the group consisting of protocatechic acid, caffeic acid, p-hydroxybenzoic acid, vanillic acid, p-coumaric acid, and ferulic acid, and mixtures thereof, present in an amount sufficient to inhibit the oxidative degradation upon exposure to air of one or more oxidative dyes present in the composition, stored in an air tight oxidation resistant metallic container.

7. The package of claim 6 wherein the air tight oxidation resistant container is aluminum having less than 100 ppm of each of cadmium, mercury, lead, and hexavalent chromium.

8. The package of claim 6 wherein the composition comprises at least one flavanoid component selected from the group consisting of aspalathin, orientin, iso-orientin, rutin, isoquercetin, vitexin, isovitexin, chryseriol, quercetin, luteolin, nothofagin, catechin and mixtures thereof; and at least one phenolic acid component selected from the group consisting of protocatechic acid, caffeic acid, p-hydroxybenzoic acid, vanillic acid, p-coumaric acid, ferulic acid and mixtures thereof.

9. The package of claim 6 wherein the at least one antioxidant has a DPPH value of greater than or equivalent to that of erythorbic acid.

10. An oxidative dye composition containing one or more oxidative dyes stabilized against oxidative degradation upon exposure to air by an organic antioxidant, wherein at least a portion of the organic antioxidant is replaced with an antioxidant comprising at least one flavanoid component and/or at least one phenolic acid component having a DPPH value greater than or equivalent to the DPPH value of the organic antioxidant that is being replaced.

11. The composition of claim 10 wherein the organic antioxidant is erythorbic acid, and wherein all of the erythorbic acid is replaced with the antioxidant comprising at least one flavanoid component and/or at least one phenolic acid component.

12. The composition of claim 11 wherein the organic antioxidant being replaced is erythorbic acid and the antioxidant that replaces the erythorbic acid is botanically derived and contains a flavanoid component comprising one or more of orientin, iso-orientin, rutin, isoquercetin, vitexin, isovitexin, chryseriol, quercetin, luteolin, nothofagin, and catechin.

13. The composition of claim 11 wherein the antioxidant that replaces the erythorbic acid is botanically derived and contains a phenolic acid component comprising one or more of pyrotocatechic acid, caffeic acid, p-hydroxybenzoic acid, vanillic acid, p-coumaric acid, and ferulic acid.

14. A method for making a multiple use oxidative dye product comprising an oxidative dye composition containing one or more oxidative dyes selected from p-phenylenediamine; p-aminophenol; o-aminophenol; N,N-bis(2-hydroxyethyl)-p-phenylenediamine; 2,5-diaminotoluene; 1-phenylamino-4-aminobenzene; 1-bis(beta-hydroxyethyl)amino-4-aminobenzene; 2,5,6-triamino-4-pyrimidinol sulfate; tetraminopyrimidine; and salts thereof; in an air tight oxidation resistant package comprising formulating the oxidative dye composition with at least one botanically derived antioxidant comprising at least one flavanoid component selected from the group consisting of aspalathin, orientin, iso-orientin, rutin, isoquercetin, vitexin, isovitexin, chryseriol, quercetin, luteolin, nothofagin, or catechin; and mixtures thereof; and at least one phenolic acid component selected from the group consisting of protocatechic acid, caffeic acid, p-hydroxybenzoic acid, vanillic acid, p-coumaric acid, and ferulic acid, and mixtures thereof, in an amount sufficient to inhibit the oxidative degradation upon exposure to air of one or more of the oxidative dyes present in the composition.

15. The method of claim 14 wherein the botanically derived antioxidant comprises aspalanthin.

16. The method of claim 14 wherein the DPPH value of the antioxidant is greater than or equivalent to that of erythorbic acid.

17. A method for making a multiple use oxidative dye product comprising an oxidative dye composition containing one or more oxidative dyes selected from p-phenylenediamine; p-aminophenol; o-aminophenol; N,N-bis(2-hydroxyethyl)-p-phenylenediamine; 2,5-diaminotoluene; 1-phenylamino-4-aminobenzene; 1-bis(beta-hydroxyethyl)amino-4-aminobenzene; 2,5,6-triamino-4-pyrimidinol sulfate; tetraminopyrimidine; and salts thereof; in an air tight oxidation resistant package comprising formulating the oxidative dye composition with at least one antioxidant comprising at least one flavanoid component and at least one phenolic acid component, in an amount sufficient to inhibit the oxidative degradation upon exposure to air of one or more of the oxidative dyes present in the composition.

18. The method of claim 17 wherein the antioxidant is botanically derived and the air tight oxidation resistant package is an aluminum tube having less than 100 ppm of each of cadium, mercury, lead, and hexavalent chromium.

19. A method for oxidatively coloring hair comprising applying to the hair an oxidative dye mixture formed by combining an oxidative dye composition comprising one or more oxidative dyes selected from selected from p-phenylenediamine; p-aminophenol; o-aminophenol; N,N-bis(2-hydroxyethyl)-p-phenylenediamine; 2,5-diaminotoluene; 1-phenylamino-4-aminobenzene; 1-bis(beta-hydroxyethyl) amino-4-aminobenzene; 2,5,6-triamino-4-pyrimidinol sulfate; tetraminopyrimidine; and salts thereof; and an aqueous oxidizing agent composition, wherein the oxidative dye mixture comprises at least one oxidative dye and at least one antioxidant botanical extract containing at least one flavanoid component selected from aspalanthin, orientin, iso-orientin, rutin, isoquercetin, vitexin, isovitexin, chryseriol, quercetin, luteolin, nothofagin; and at least one phenolic acid component selected from protocatechic acid, p-hydroxybenzoic acid, vanillic acid, p-coumaric acid, ferulic acid, and mixtures thereof.

20. The method of claim 19 wherein the mixture is applied to hair for 5 to 60 minutes.

21. The composition of claim 5 wherein the extract is present in an amount ranging from about 0.0001 to 35% by weight.

22. The composition of claim 21 wherein the oxidative dye comprises at least one primary intermediate and at least one coupler for the formation of oxidation dyes.

23. The composition of claim 22 wherein the primary intermediate is selected from p-phenylenediamine; p-aminophenol; o-aminophenol; N,N-bis(2-hydroxyethyl)-p-phenylenediamine; 2,5-diaminotoluene, tetraminopyrimidine; and salts thereof.

24. The composition of claim 22 wherein the coupler is selected from m-aminophenol; 2,4-diaminotoluene; 4-amino-2-hydroxytoluene; phenyl methylpyrazolone; 1,3-diaminobenzene; 6-methoxy-1,3-diaminobenzene; 1-naphthol; resorcinol; and mixtures thereof.

25. The composition of claim 22 wherein the oxidative dye composition further comprises at least one surfactant.

* * * * *